(12) United States Patent
Segman

(10) Patent No.: US 9,855,009 B2
(45) Date of Patent: Jan. 2, 2018

(54) APPARATUS FOR MEASURING BLOOD CHARACTERISTICS FOR DEPLOYMENT ON A HOST DEVICE HAVING A DIGITAL SENSOR

(75) Inventor: Yosef Segman, Zichron Yaakov (IL)

(73) Assignee: CNOGA MEDICAL LTD., Or Akiva (IL)

( * ) Notice: Subject to any disclaimer, the term of this patent is extended or adjusted under 35 U.S.C. 154(b) by 258 days.

(21) Appl. No.: 13/549,481

(22) Filed: Jul. 15, 2012

(65) Prior Publication Data

US 2014/0018647 A1    Jan. 16, 2014

(51) Int. Cl.
*A61B 5/1455* (2006.01)
*A61B 5/00* (2006.01)

(52) U.S. Cl.
CPC ........ *A61B 5/6898* (2013.01); *A61B 5/14552* (2013.01); *A61B 5/683* (2013.01); *A61B 5/6826* (2013.01); *A61B 2560/0443* (2013.01)

(58) Field of Classification Search
CPC .......................... A61B 5/14551; A61B 5/1455

USPC .................................................. 600/310–344
See application file for complete search history.

(56) References Cited

U.S. PATENT DOCUMENTS

| 2009/0137891 A1* | 5/2009 | Wang ............................ 600/384 |
| 2009/0203998 A1* | 8/2009 | Klinghult et al. ............ 600/443 |
| 2012/0323096 A1* | 12/2012 | Yu et al. ....................... 600/340 |

* cited by examiner

*Primary Examiner* — Eric Winakur
*Assistant Examiner* — Marjan Fardanesh
(74) *Attorney, Agent, or Firm* — Mark M. Friedman

(57) ABSTRACT

An apparatus for working in conjunction with a digital sensor, CPU and display of a host device in order to measure blood characteristics that includes a housing configured for association with the host device so as to define between them a chamber into which at least a portion of an appendage of a living being is placed such that a tip of the appendage is deployed adjacent to the digital sensor so as to cover the digital sensor. The chamber substantially encloses the digital sensor. Light from a light source is directed toward the appendage tip, wherein at least some light from the light source is reflected by tissue of the appendage, is received by the sensor and data thereby generated is processed by the CUP to determine the blood characteristics.

15 Claims, 3 Drawing Sheets

APPARATUS FOR MEASURING BLOOD CHARACTERISTICS FOR DEPLOYMENT ON A HOST DEVICE HAVING A DIGITAL SENSOR

FIELD AND BACKGROUND OF THE INVENTION

The present invention relates to devices for measuring blood characteristics and, in particular, it concerns an apparatus for measuring, or determining, blood characteristics for deployment on a host device having a digital sensor, Central Processing Unit and display.

It is known to provide devices for measuring blood characteristics by passing light through a portion of a living body, such as a human finger tip. Such a device is described in U.S. patent application Ser. No. 12/260,251, Finger Deployed Device for Measuring Blood and Physiological Characteristics, the disclosure of which is incorporated herein in its entirety by this reference.

Such devices, however, are relatively expensive because they are all inclusive and therefore include a housing, light source, a digital sensor, a Central Processing Unit (CPU) and display.

There are numerous consumer devices in use today that include a digital sensor, a CPU and display. Such devices include, but are not limited to, cellular telephone, digital cameras and computers having either a built-in camera or the ability to have a digital camera attached such as by a USB port. Any of these devices therefore, can act as host a device for as apparatus that utilizes the existing digital sensor, CPU and display.

There is therefore a need for an apparatus for measuring blood characteristics for deployment on a host device having a digital sensor, Central Processing Unit and display.

SUMMARY OF THE INVENTION

The present invention is an apparatus for measuring blood characteristics for deployment on a host device having a digital sensor, Central Processing Unit and display.

According to the teachings of the present invention there is provided, an apparatus for working in conjunction with a digital sensor, CPU and display of a host device in order to measure blood characteristics, the apparatus comprising, a housing configured for association with the host device so as to define between them a chamber, which substantially encloses the digital sensor, into which at least a portion of an appendage of a living being is placed such that a tip of said appendage is deployed adjacent to the digital sensor so as to cover the digital sensor and light from a light source is directed toward said appendage tip, wherein at least some light from said light source is reflected by tissue of said appendage, is received, by the sensor and data thereby generated is processed by the CUP to determine the blood characteristics.

According to the teachings of the present invention, said light source is included in said housing.

According to the teachings of the present invention, said housing includes two side walls, an end wall and a cover of said chamber and the host device includes a bottom of said chamber.

According to the teachings of the present invention, said cover is hingedly attached to said housing.

According to the teachings of the present invention, said association between said housing and the host device is a detachable connection of the apparatus to the host device.

According to the teachings of the present invention, said housing is configured to be interchangeably deployable on at least some of: a cellular telephone, a digital camera, a webcam connected to a computer, a computer having in integral webcam.

According to the teachings of the present invention, said light source is a powered light source configured in said housing.

According to the teachings of the present invention, said light source is powered by at least one of the host device, an internal battery and a photovoltaic cell.

There is also provided according to the teaching of the present invention, a method for determining blood characteristics using an apparatus working in conjunction with a digital sensor, CPU and display of a host device, the method comprising: (a) providing the CPU with a program for analyzing blood characteristics; (b) providing an apparatus having housing configured for association with the host device; (c) providing a light source; (d) associating said housing with said host device so as to define between them a chamber into which at least a portion of an appendage of a living being is placed, said chamber substantially enclosing the digital sensor; (e) placing said at least a portion of an appendage in said chamber such that a tip of said appendage is deployed adjacent to the digital sensor so as to cover the digital sensor; (f) directing light from said light source toward said tip of said appendage such that at least some light from said light source is reflected by tissue of said appendage; (g) receiving at least some of said reflected light by the digital sensor; and (h) analyzing data thereby generate is processed by the CUP to determine the blood characteristics.

According to the teachings of the present invention, there is also provided emitting light from said light source, wherein said light source is a powered light source.

According to the teachings of the present invention, there is also provided providing power to said light source from at least one of: the host device, an internal battery and a photovoltaic cell.

According to the teachings of the present invention, said housing is configured to provide at least three sides and a cover of said chamber and the host device provides a bottom of said chamber.

According to the teachings of the present invention, said cover is implemented so as to be hingedly attached to said housing.

According to the teachings of the present invention, said association between said housing and the host device is implemented as a detachable connected of the apparatus to the host device.

According to the teachings of the present invention, said housing is implemented so as to be interchangeably deployable on at least some of: a cellular telephone, a digital camera, a webcam connected to a computer, a computer having in integral webcam.

According to the teachings of the present invention, said receiving is implemented such that said digital sensor produces images of spatial-temporal color pixel information acquired by said light being reflected from said light source into said appendage tip capillary tissue.

According to the teachings of the present invention, said data includes said spatial-temporal color pixel information so as to determine bio chemical parameters and hemodynamic parameters.

According to the teachings of the present invention, there is also provided displaying a result of said analyzing on a display unit of the host device.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
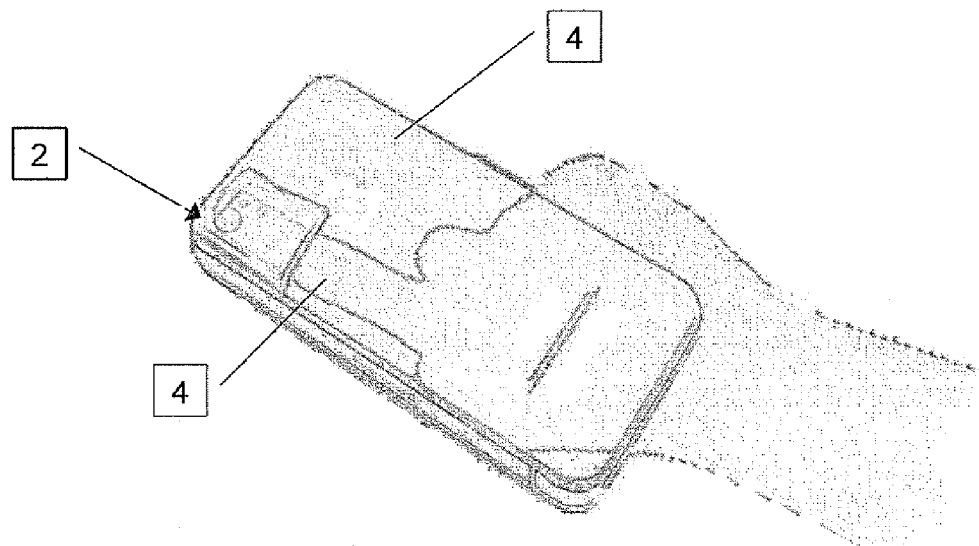
FIG. 1 is an isometric view of the apparatus of the present invention deployed on a cellular telephone and being used on a human finger.

The present invention is an apparatus for measuring blood characteristics for deployment on a host device having a digital sensor and

Central Processing Unit

The principles and operation of an apparatus for measuring blood characteristics according to the present invention may be better understood with reference to the drawings and the accompanying description.

By way of introduction, as mentioned above, stand alone devices for measuring blood characteristics by passing light through a portion of a living body, such as a human finger are known. All of these devices include at least a digital sensor and a CPU and usually a display unit as well.

There is also a growing sophistication of devices such as, but not limited to, cellular telephones (especially Smartphones as illustrated herein), digital still or video cameras and computers having either a built-in camera or the ability to have a digital camera attached such as by a USB port, and "Apps" to be downloaded and run on these devices. Any of these devices therefore, can act as host a device for as apparatus that utilizes the existing digital sensor, CPU and display of the host device.

As used herein, the phrase "host device" refers to substantially any device having a CPU and a digital imaging sensor (hereafter digital sensor) either built-in (integral) or attached/attachable thereto, such as those listed immediately above.

The present invention is an apparatus to be used in association with such a host device for measuring or determining blood characteristics. In order to do as, a user simply downloads/installs the necessary software/App. The apparatus of the present invention is associated with, the host device so as to cover the host device's digital sensor. Such association may include detachable connection of the apparatus to the host device, as will discussed in more detail below. Alternatively, the apparatus housing may be deployed directly on an appendage of the user such as a finger, or toe, and manually held against the host device in a position covering the digital sensor.

The housing of the apparatus is configured with a light source, which may be as simple as a hole in the end wall 16 which allows ambient light to enter the chamber. When configured thusly, the hole may include a lens for directing and/or amplifying the ambient light. It will be appreciated that the ambient light may be naturally occurring such as, but not limited to, sun light. Alternatively, the ambient light may be supplied by a man-made light emitting device such as, but on limited to, incandescent light bulbs, florescent light bulbs, LED lights and laser lights.

Preferably, however, the light source is powered and may be a single element or an array of elements such as, but not limited to, LEDs that is preferably mounted on the inside surface of the end wall 16. In this configuration, the light source may be powered by, but not limited to, an electrical connection to the host device or independently by means of an internal battery or a photovoltaic cell (90 in FIG. 3), by non-limiting example. It will be understood that such a powered light source requires a control unit. Such a control unit (not shown) may be located in either the apparatus cover, side walls or end wall.

Alternatively, an detached light source may be deployed directly on the host device while being controlled by the apparatus of the present invention.

If the host device includes a flash unit, the host flash may be used as the light source for the present invention.

The digital sensor of the host device produces images of spatial-temporal color pixel information acquired from light that is emitted by the light source and reflected by the finger tip capillary tissue. The spatial-temporal color pixel information is used to compute bio chemical parameters and hemodynamic parameters by the host device CPU. The results are displayed on the host device's display unit.

Referring now to the drawings, FIG. 1 illustrates the apparatus 2 deployed on a Smartphone 4, thereby forming a chamber into which a human finger 6 is inserted.

Figure 2:
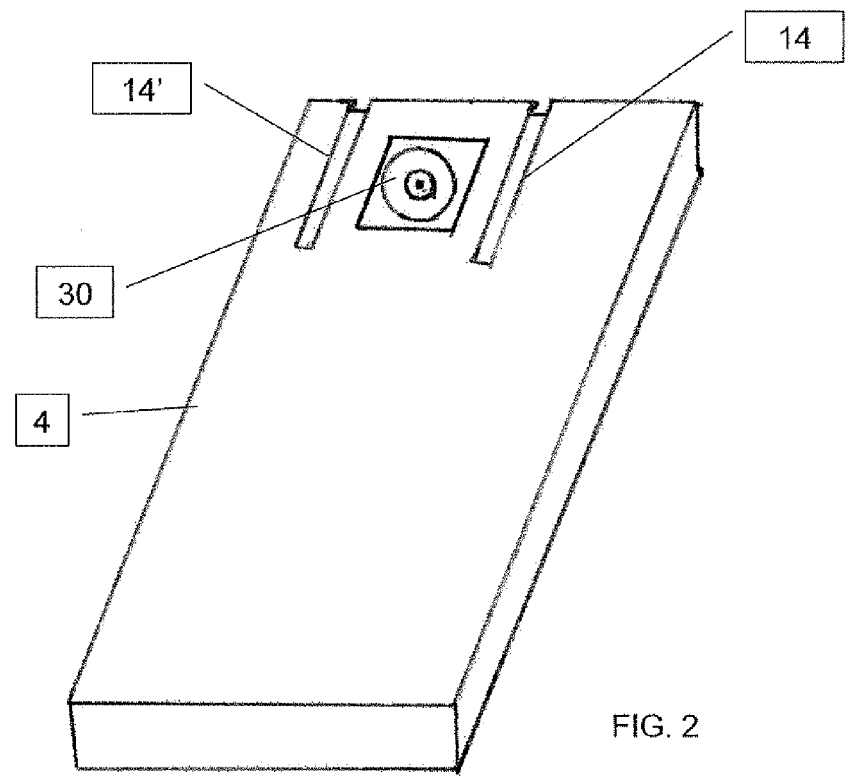
FIG. 2 is an isometric view of a cellular telephone modified to accept deployment of the apparatus of the present invention.
Figure 3:
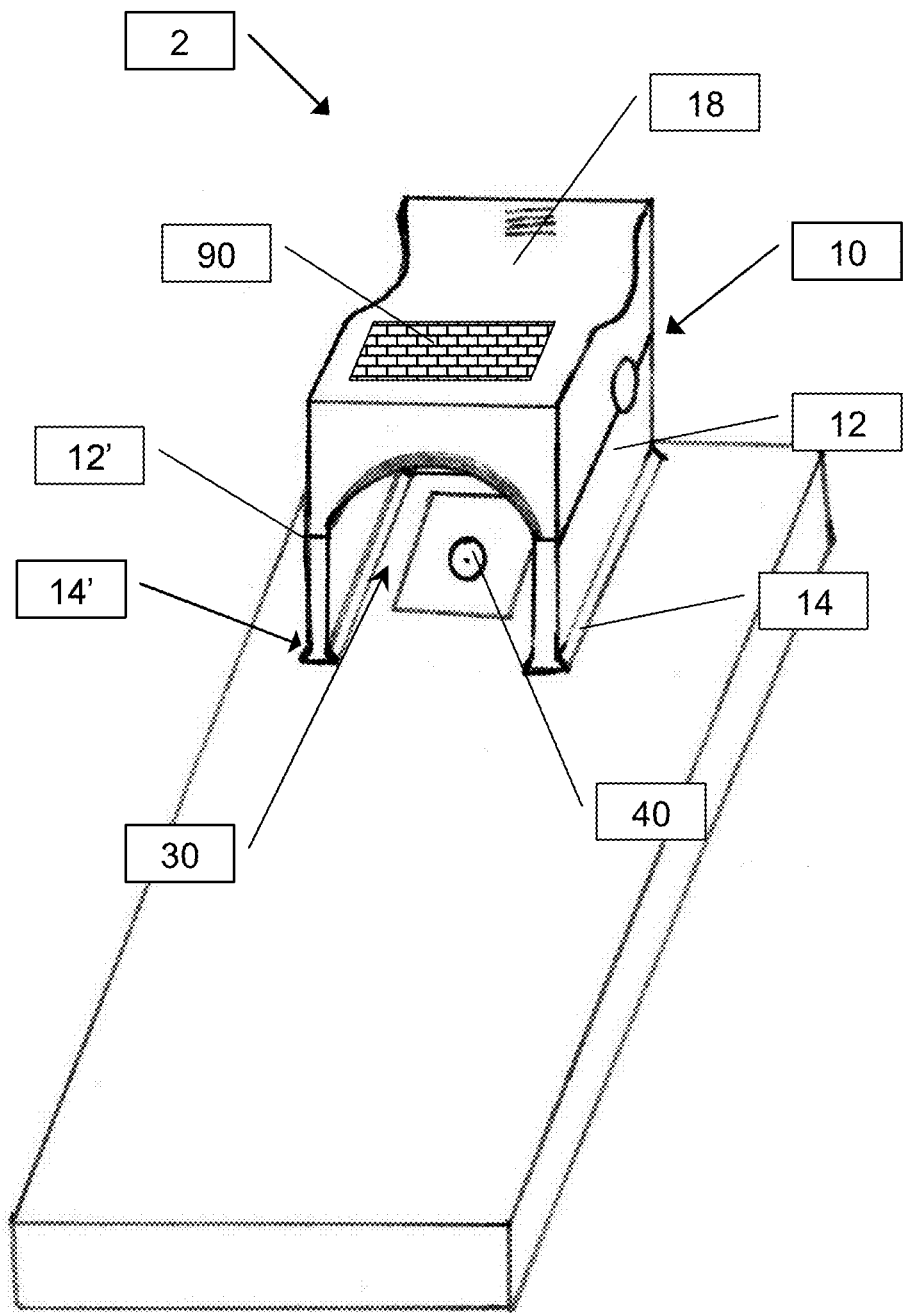
FIG. 3 is an isometric view of the cellular telephone of FIG. 2 shown here after deployment of the apparatus of the present invention.

FIGS. 2 and 3 illustrated one example of a detachable connection between the host device 4 and the housing 10 of the apparatus 2. In the illustration here, the connection is achieved by matingly sliding the parallel side walls 12 and 12' on the apparatus housing 10 into the grooves 14 and 14' configured in the host device 4. It will be appreciated that such grooves may be configured in a protective cover for the host device, such protective covers being in common use. It will also be appreciated that the connection of the apparatus of the present invention and the host device may be achieved by substantially any suitable means known such as, but not limited to, hook and loop arrangements, clamps, clips and elastic bands, all of which may interact directly with the host device, or alternatively with a protective cover deployed on the host device.

Figure 4:
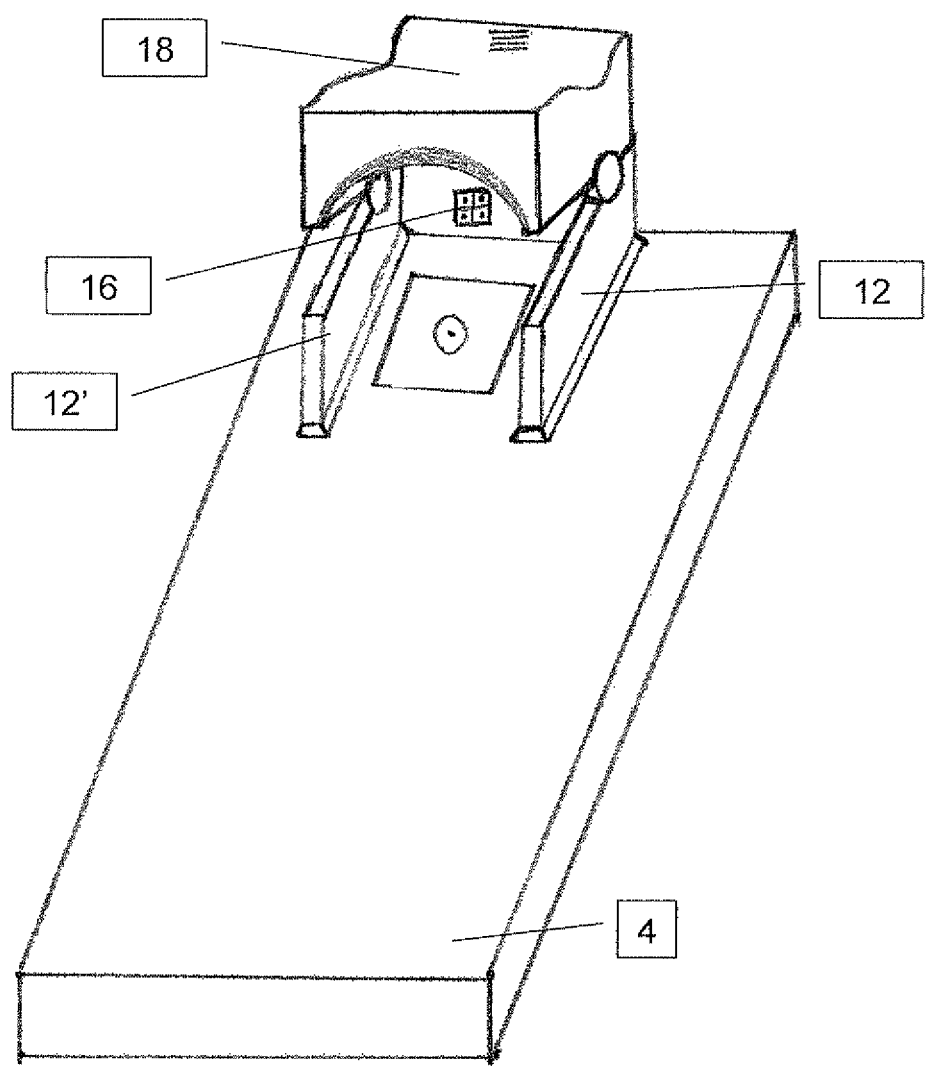
FIG. 4 is an isometric view of the cellular telephone of FIG. 2 shown here the apparatus of the present invention deployed with the hinged lid in an open position.

As seen in FIG. 3, the apparatus housing 10 includes two side walls 12 and 12', an end wall 16 and a cover 18. As illustrated in FIG. 4, cover 18 may be hingedly attached to the housing 10 so as to facilitate insertion of the finger into the chamber 30 that is defined by the housing 10 and a portion of the host device 4. Note that the digital camera 40 of the host device 4, which will act as the digital sensor, is located inside of, and substantially enclosed within, chamber 30 when the apparatus housing 10 is deployed on the host device 4.

FIG. 4 comes to illustrate the hinged configuration of housing cover 18 and further shows the end wall 16 and the light source 20.

The present invention also provides a method for using the apparatus. The method includes the steps of:

(1) Providing the CPU of the host device with a program for analyzing blood characteristics;

(2) Providing an apparatus having housing configured for association with the host device;

(3) Providing a light source;

(4) Associating the housing with the host device so as to define between them a chamber into which at least a portion of an appendage of a living being is placed, the chamber substantially enclosing the digital sensor;

(5) Placing the at least a portion of an appendage in the chamber such that a tip of the appendage is deployed adjacent to the digital sensor so as to cover the digital sensor;

(6) Directing light from the light source toward the tip of the appendage such that at least some light from the light source is reflected by tissue of the appendage;

(7) Receiving at least some of the reflected light by the digital sensor;

(8) Analyzing data thereby generated is processed by the CUP to determine the blood characteristics; and (9) Displaying the results on the display unit of the host device.

It will be appreciated that the above descriptions are intended only to serve as examples and that many other embodiments are possible within the spirit and the scope of the present invention.

What is claimed is:

1. An apparatus configured for use with a digital sensor, CPU and display of an external host device, having a digital sensor, CPU and display in order to measure blood characteristics, the apparatus comprising:
   a housing having an end wall, a first side wall, a second side wall, a cover, a bottom edge of at least one of the first and second side walls is adapted for releasable attachment to the host device so as to define between said housing and the host device, when the apparatus is attached to the host device, a chamber, which substantially encloses the digital sensor, into which at least a portion of a finger of a living mammalian subject is placed such that a tip of said finger is deployed adjacent to the digital sensor so as to cover the digital sensor and light from a light source is directed toward said finger tip, such that at least some light from said light source interacts with tissue of said finger, is received by the sensor and data thereby generated is processed by the CPU to determine the blood characteristics, wherein said releasable attachment of said housing is a detachable connection such that said housing is removable from the host device,
   the light source mounted on the end wall so as to direct light axially at the tip of the finger in the chamber, wherein the cover is configured to rotate outward upon entry of the at least a portion of the finger into the chamber.

2. The apparatus of claim 1, wherein said first and, second side walls are parallel to one another.

3. The apparatus of claim 2, wherein said cover is hingedly attached to said housing.

4. The apparatus of claim 1, wherein said housing is configured to be interchangeably deployable on at least some of: a cellular telephone, a digital camera, a webcam connected to a computer, a computer having in integral webcam.

5. The apparatus of claim 1, wherein said light source is a powered light source mounted on an inside surface of an end wall of said housing.

6. The apparatus of claim 5, wherein said light source is powered by at least one of: the host device, an internal battery and a photovoltaic cell.

7. A method for determining blood characteristics using an apparatus configured for use in conjunction with a digital sensor, CPU and display of a host device, the method comprising:
   (a) providing the CPU with a program for analyzing blood characteristics;
   (b) providing an apparatus having a housing having an end wall, a first side wall, a second side wall, a cover, a bottom edge of at least one of the first and second side walls is adapted for releasable attachment to the host device, wherein said releasable attachment of said housing is a detachable connection such that said housing is removable from the host device, wherein the cover is configured to rotate outward upon entry of the at least a portion of the finger into the chamber;
   (c) providing a light source mounted on said end wall;
   (d) attaching said housing to said host device so as to define between said housing and said host device a chamber into which at least a portion of a finger of a living mammalian subject is placed, said chamber substantially enclosing the digital sensor;
   (e) placing said at least a portion of said finger in said chamber such that a tip of said finger is deployed adjacent to the digital sensor so as to cover the digital sensor;
   (f) directing light from said light source axially at said tip of said finger such that at least some light from said light source interacts with tissue of said finger;
   (g) receiving at least some of said light by the digital sensor; and
   (h) analyzing data generated by the digital sensor, using the CPU, to determine the blood characteristics.

8. The method of claim 7, further including emitting light from said light source, wherein said light source is implemented as a powered light source mounted on an inside surface of said end wall of said housing.

9. The method of claim 8, further including providing power to said light source from at least one of: the host device, an internal battery and a photovoltaic cell.

10. The method of claim 7, wherein said housing is implemented with two side walls that are parallel to one another.

11. The method of claim 10, wherein said cover is implemented so as to be hingedly attached to said housing.

12. The method of claim 7, wherein said housing is implemented so as to be interchangeably deployable on at least some of: a cellular telephone, a digital camera, a webcam connected to a computer, a computer having in integral webcam.

13. The method of claim 7, wherein said receiving is implemented such that said digital sensor produces images of spatial-temporal color pixel information acquired by said light being reflected from said light source into said appendage tip capillary tissue.

14. The method of claim 13, wherein said data includes said spatial-temporal color pixel information so as to determine bio chemical parameters and hemodynamic parameters.

15. The method of claim 7, further including displaying a result of said analyzing on a display unit of the host device.

* * * * *